United States Patent
Fischer et al.

(10) Patent No.: US 9,622,768 B2
(45) Date of Patent: Apr. 18, 2017

(54) WATER JET SURGICAL INSTRUMENT

(75) Inventors: Klaus Fischer, Nagold (DE); Daniel Schaeller, Tuebingen (DE); Matthias Voigtlaender, Gomaringen (DE); Mara Szyrach, Zurich (CH); Irina Sigle, Moessingen (DE); Lars Blobel, Ammerbuch-Entringen (DE); Markus Enderle, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 197 days.

(21) Appl. No.: 12/935,986

(22) PCT Filed: Mar. 31, 2009

(86) PCT No.: PCT/EP2009/002343
§ 371 (c)(1),
(2), (4) Date: Oct. 12, 2010

(87) PCT Pub. No.: WO2009/121563
PCT Pub. Date: Oct. 8, 2009

(65) Prior Publication Data
US 2011/0028887 A1 Feb. 3, 2011

(30) Foreign Application Priority Data
Apr. 3, 2008 (DE) .................. 10 2008 017 066
May 27, 2008 (DE) .................. 10 2008 025 233

(51) Int. Cl.
A61B 17/3203 (2006.01)
A61B 17/00 (2006.01)
A61B 17/34 (2006.01)

(52) U.S. Cl.
CPC .... *A61B 17/3203* (2013.01); *A61B 17/32037* (2013.01); *A61B 17/3478* (2013.01);
(Continued)

(58) Field of Classification Search
CPC .......... A61B 17/3203; A61B 17/32037; A61B 2017/00818; A61B 2017/00269; A61B 17/3478
(Continued)

(56) References Cited

U.S. PATENT DOCUMENTS 5,536,242 A * 7/1996 Willard et al. .................. 604/30
5,944,686 A    8/1999 Patterson et al.
(Continued)

FOREIGN PATENT DOCUMENTS

CN         101155555 A      4/2008
DE   20 2005 009 717 U1   12/2006
(Continued)

OTHER PUBLICATIONS

English translation WO 2006/108480, Endoscopic Surgical Instrument.*

*Primary Examiner* — Anh Dang
(74) *Attorney, Agent, or Firm* — Blank Rome LLP (57) ABSTRACT

A water jet surgical instrument including a supply line for supplying a cutting fluid and a discharge nozzle for forming and discharging a fluid jet, wherein the fluid jet has a predetermined spread angle and/or a predetermined emergence energy. A jet shaping device is arranged relative to the discharge nozzle such that the fluid jet is able to be adjusted by the jet shaping device with regard to the spread angle and/or emergence energy thereof.

19 Claims, 7 Drawing Sheets

(52) U.S. Cl.
CPC ............... *A61B 2017/00269* (2013.01); *A61B 2017/00818* (2013.01)

(58) Field of Classification Search
USPC ............ 606/106, 159, 167, 131; 604/22, 24, 604/68–72
See application file for complete search history.

(56) References Cited

U.S. PATENT DOCUMENTS

| | | |
|---|---|---|
| 6,135,977 A | 10/2000 | Drasler et al. |
| 6,196,989 B1 | 3/2001 | Padget et al. |
| 6,641,553 B1 | 11/2003 | Chee et al. |
| 6,942,649 B2 | 9/2005 | Ignon et al. |
| 2002/0063170 A1 | 5/2002 | Pein |
| 2003/0073902 A1 | 4/2003 | Hauschild et al. |
| 2004/0186384 A1* | 9/2004 | Babaev ........................ 600/489 |
| 2004/0243157 A1* | 12/2004 | Connor et al. ................ 606/159 |
| 2006/0142690 A1* | 6/2006 | Pratt ............................. 604/23 |
| 2007/0219481 A1* | 9/2007 | Babaev .......................... 604/22 |

FOREIGN PATENT DOCUMENTS

| | | |
|---|---|---|
| DE | 10 2007 002 486 A1 | 7/2008 |
| EP | 0 691 183 A1 | 1/1996 |
| EP | 1 199 054 A1 | 4/2002 |
| EP | 1 929 968 A1 | 6/2008 |
| JP | 1-313048 A | 12/1989 |
| JP | 5-35281 B2 | 5/1993 |
| JP | H06-205831 A | 7/1994 |
| WO | WO 96/39953 A1 | 12/1996 |
| WO | WO 00/59386 A1 | 10/2000 |
| WO | WO 02/053014 A2 | 7/2002 |
| WO | WO 2004/014460 A2 | 2/2004 |
| WO | WO 2006/108480 A1 | 10/2006 |

\* cited by examiner

WATER JET SURGICAL INSTRUMENT

FIELD OF THE DISCLOSED EMBODIMENTS

The disclosed embodiments relate to a water jet surgical instrument including a supply line for supplying a cutting fluid and a discharge nozzle for forming and discharging a fluid jet, wherein the fluid jet has a predetermined spread angle and/or a predetermined emergence energy.

BACKGROUND

During resection of tissue, particularly of tumor tissue in the gastrointestinal tract, that is restricted to the mucosa, excision should be carried out, where possible, in one session and as fully as possible. Conventionally, for this purpose, the snare technique or the cap technique are used, wherein, depending on the snare diameter or the cap diameter, circular excisions of varying size are produced.

In order to be able to excise large-area tumours with a diameter of more than eight centimeters in one session and as completely as possible, it is proposed, for example, in WO 2006/108480 A1 that, during endoscopic mucosa resection, fluid is first injected under the mucosa through a flexible needle before the resection. For this, the needle is inserted into the submucosa. Due to the penetration of the fluid into the mucosa, it becomes separated from the muscularis propria, so that a fluid cushion is produced under the mucosa. This creates a safe separation from the muscularis propria as well as provides thermal protection. The mucosa resection is then performed using, for example, a flexible discission needle, and particularly a high-frequency surgical instrument. Alternatively, the prior art also discloses resection by means of argon plasma coagulation.

With the water jet surgical instrument of the prior art, a concentrated water jet emerges at the distal end of the instrument under high pressure and penetrates the soft mucosa. In the submucosa (in the elastic fibrous displaceable layer) the penetrating fluid collects so that a fluid cushion is produced. For this type of selective tissue separation according to the prior art, a fluid jet with a high water flow rate and a high speed is used. Due to the geometry, a laminar water jet having the diameter of the nozzle is produced at the nozzle outlet.

It is considered problematic that during endoscopic submucosal dissection of this type, a perforation of the muscularis propria (referred to simply as 'muscularis' below) by the water jet can occur. This, in turn, can lead to dangerous internal bleeding which also hinders the view of the surgeon, so that rinsing of the operation site has to be carried out. This requires removal of the instrument from the operating channel, which involves further delay and further risk to the patient.

SUMMARY

The disclosed embodiments provide a water jet surgical instrument which facilitates tissue resection and, in particular, reduces the risk of perforation of the muscularis and internal bleeding.

Disclosed embodiments include a water jet surgical instrument including a supply line for supplying a cutting fluid and a discharge nozzle for shaping and discharging a fluid jet with a predetermined spread angle and/or a predetermined emergence energy. A jet shaping device is also provided and is arranged relative to the discharge nozzle such that the spread angle and/or emergence energy of the fluid jet is able to be adjusted by the jet shaping device.

Due to the variation of the spread angle and/or the emergence energy of the fluid jet, the water jet surgical instrument of the disclosed embodiments can be adapted to use with a particular tissue. In this way, for example, the different tissue thicknesses in the esophagus, stomach, colon and rectum can be taken into account by adjusting the pressure of the fluid jet to the respective tissue. Variation of the spread angle has the further advantage that the extent of a tumor to be removed can be made visible with a staining medium, such as methylene blue or the like, at the beginning of an endoscopic submucosal dissection.

Preferably, the jet shaping device is adjustable in the position thereof relative to the discharge nozzle to set the spread angle and/or the emergence energy, thereby ensuring particularly simple and uncomplicated setting of the spread angle and/or the emergence energy.

In a further embodiment, the jet shaping device is mounted in a preferably flexible sheathing tube. The construction effort associated with a design of this type is particularly slight.

The jet shaping device of the water jet surgical instrument may also include a swirl element, which adds a twisting flow to the fluid jet to spread said jet and/or to reduce the emergence energy thereof. In this way, the spread and/or the emergence energy of the fluid jet can be adjusted in particularly easy manner.

The jet shaping device of the water jet surgical instrument may also include a deflecting element, which can be positioned projecting at least partially into the fluid jet in order to deflect or spread said jet and/or to reduce the emergence energy thereof, or to allow through an unchanged fluid jet. A deflecting element of this type is particularly easy to produce.

The jet shaping device may also include an air feed device and/or fluid feed device, which feeds air and/or fluid into the fluid jet in order to deflect and/or spread said jet and/or to reduce the emergence energy thereof. A design of this type is advantageous if displacement of large parts of the jet shaping device is to be avoided or reduced.

In one preferred embodiment, the jet shaping device of the water jet surgical instrument comprises a Venturi nozzle for mixing in a gas or a liquid. In this way, gas or a liquid can be easily mixed in with the fluid jet in precise proportions.

The water jet surgical instrument may also be configured for rinsing out an operation site and/or for cleaning an image recording device of an endoscope. In this way, several functions of the water jet surgical instrument are suitably combined in one instrument and the operation is made easier.

Preferably, the water jet surgical instrument is configured to be insertable into an endoscope (e.g., within a working channel), enabling endoscopic operations.

In another preferred embodiment, a nozzle spacer is associated with the discharge nozzle of the water jet surgical instrument to vary the distance of the discharge nozzle from a tissue to be treated. This also simplifies utilization of the instrument.

BRIEF DESCRIPTION OF THE DRAWINGS

The disclosed embodiments will now be described in greater detail, pointing out further features and advantages by reference to exemplary embodiments as illustrated in the drawings.

DETAILED DESCRIPTION

Figure 1:
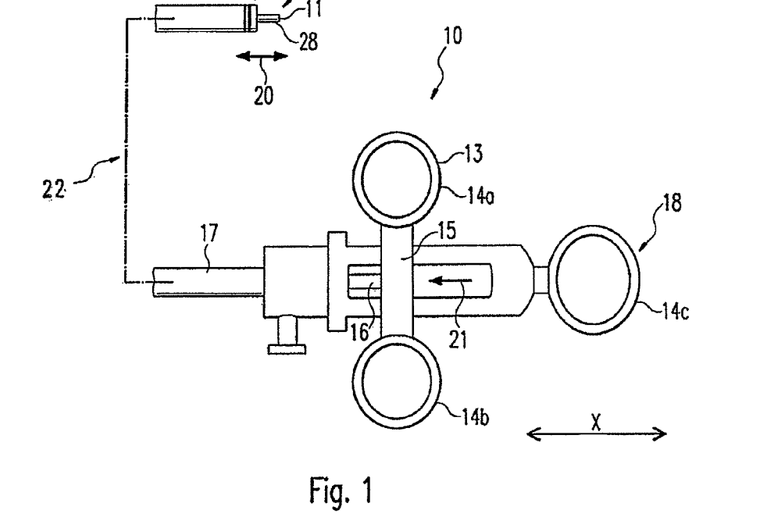
FIG. 1 is a schematic representation of a water jet surgical instrument according to the disclosed embodiments.

FIG. 1 shows a water jet surgical instrument 10, wherein a cutting fluid can be fed via a supply line 22 to a discharge nozzle 11. At the discharge nozzle 11, which is arranged at a distal end 19, a water jet 2 (see FIG. 3) emerges, which is adjustable by means of a jet shaping device 12 with regard to the spread angle α and emergence energy thereof. The jet shaping device 12 is only suggested in FIG. 1 and is shown in more detail in FIGS. 4 to 25 in various embodiments.

The jet shaping device 12 is adjusted or controlled via an adjusting element 13. The adjusting element 13 includes three grip elements 14a, 14b, 14c, wherein the grip element 14c is arranged at a proximal end 18 of the water jet surgical instrument 10. The grip elements 14a and 14b are connected to one another via a transverse connection 15, wherein this transverse connection 15 is also firmly connected to a shaft 16.

The hollow shaft 16 which includes a supply line 22 is guided within a flexible sheathing tube 17 and can be displaced in a longitudinal direction X of the water jet surgical instrument 10. The shaft 16 also includes a shaft end piece 28, on which the discharge nozzle 11 is arranged. The discharge nozzle 11 is therefore always regarded below as being a component part of the shaft 16 and does not necessarily have to include a discharge aperture of the jet shaping instrument.

The adjusting element 13, which is firmly connected to the shaft 16, is configured such that a thumb can be inserted into the grip element 14c and the index finger and ring finger of the same hand can be inserted into the grip elements 14a and 14b, so that with a spreading movement of the fingers, the shaft 16 is moved in the direction of the distal end 19, whereas pulling the fingers together leads to a movement in the direction of the proximal end 18.

The arrows 20 and 21 indicate the movement of the shaft 16 together with the transverse connection 15 and the grip elements 14a and 14b (arrow 21) and the associated corresponding movement of the supply line 22 or of the discharge nozzle 11 (arrow 20).

In the event that the water jet surgical instrument 10 is configured to be combined with or structurally integrated with a high-frequency device, the shaft 16 preferably also includes an active electrode of the high-frequency device.

Figure 2:
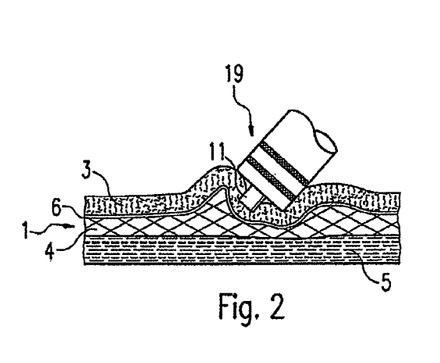
FIG. 2 is a schematic representation of a distal end of the water jet surgical instrument of FIG. 1, before the injection of fluid into the submucosa.

FIG. 2 shows the distal end 19 of the water jet surgical instrument 10, wherein the discharge nozzle 11 is pressed against the mucosa 3 of a tissue 1. FIG. 2 illustrates the condition of the tissue 1 before the injection of fluid into the submucosa 4. The distance of the discharge nozzle 11 from the muscularis 5 is extremely small, so that the fluid jet 2 (see FIG. 3), particularly a concentrated laminar fluid jet (as previously described with respect to prior art devices), can pass through the respective tissue layers, specifically the mucosa 3, the submucosa 4 and the muscularis (propria) 5 with a high kinetic energy. It can therefore also occur that the muscularis 5 becomes perforated, which is both undesirable and highly injurious to the patient.

Figure 3:
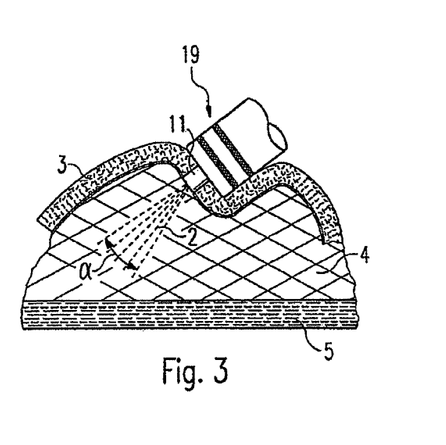
FIG. 3 is a schematic representation of the distal end in FIG. 2 of the water jet surgical instrument of FIG. 1 during or following injection of fluid into the submucosa.

FIG. 3 shows the distal end 19 of the water jet surgical instrument 10, wherein the discharge nozzle 11 is lightly pressed into the mucosa. In disclosed embodiments, the fluid jet 2 may be spread by an angle α, so that the energy density of the fluid jet 2 impinging upon the muscularis 5 is so small that a perforation of the muscularis 5 is now (practically) impossible. Fluid is injected under the submucosa 4 in the desired manner and without causing injury to the patient. It is important in this regard that the angle α of the fluid jet 2 can be adapted to the prevailing conditions in order to vary the energy density of the jet impacting upon the muscularis. For example, a different angle α is set for treatment of tissue layers in the esophagus than for treatment in the stomach, colon or rectum.

Figure 4:
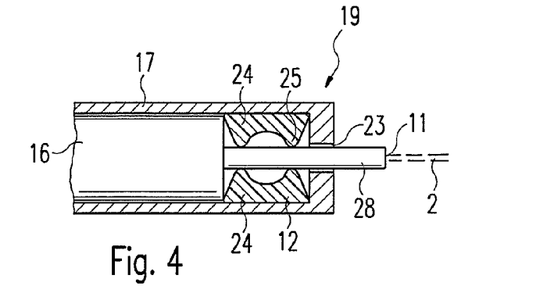
FIG. 4 is a schematic representation of an embodiment of the water jet surgical instrument (distal end) in a first adjustment position.
Figure 5:
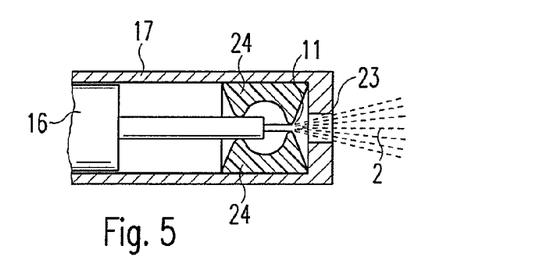
FIG. 5 is a schematic representation of the embodiment of FIG. 4 in a second adjustment position.

FIG. 4 shows a first embodiment of the jet shaping device 12 (distal end 19 only). In this case, the jet shaping device 12 comprises an elastic element 24 with lip-like projections 25. In FIG. 4, the shaft 16 is pushed in the direction of the distal end 19 in such a manner that the discharge nozzle 11, which in this case discharges a laminar fluid jet 2, is situated outside the sheathing tube 17. The discharge nozzle 11 therefore also comprises the discharge aperture in this case. In FIG. 5, the shaft 16 is withdrawn in such a manner that the discharge nozzle 11 comes to lie between the projections 25. The laminar fluid jet 2 emerging from the discharge nozzle 11 is thereby shaped or spread relative to the jet 2 in FIG. 4 by the form of the projections 25 which lie closer to the distal end 19, and the sheathing tube aperture 23. In this case, the sheathing tube aperture 23 functions as a discharge aperture. When the discharge nozzle 11 is withdrawn, the jet is spread, whereas when the discharge nozzle is pushed out, the jet is made narrower.

Figure 6:
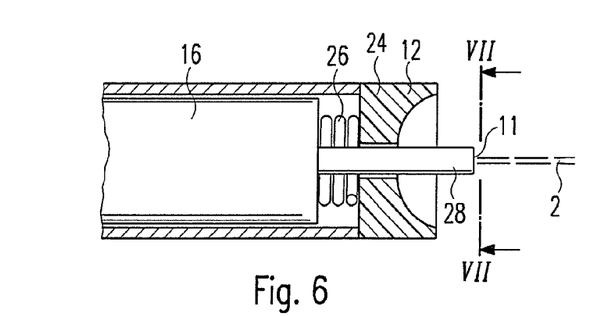
FIG. 6 is a schematic representation of another embodiment of the water jet surgical instrument (distal end) in a first adjustment position.
Figure 7:
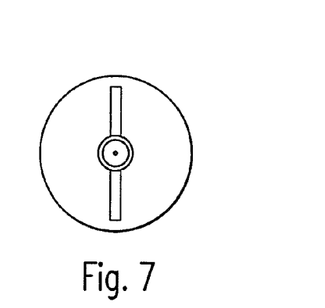
FIG. 7 is a cross-sectional view through the fluid jet along the line VII-VII, in FIG. 6.
Figure 8:
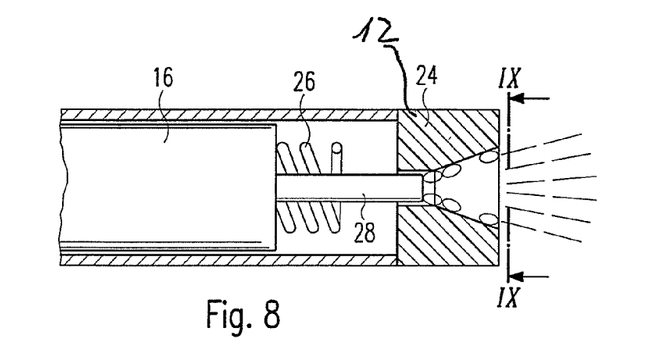
FIG. 8 is a schematic representation of the embodiment of FIG. 6 in a second adjustment position.
Figure 9:
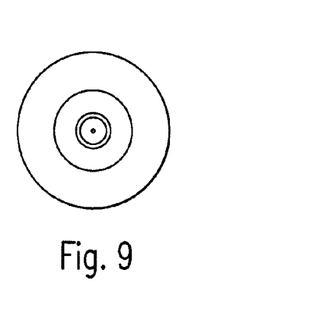
FIG. 9 is a cross-sectional view through the fluid jet along the line IX-IX in FIG. 8.

In FIG. 6 and FIG. 8, another embodiment of the jet shaping device 12 is shown. In FIG. 6, the shaft 16 is in a position such that a spring element 26 applies pressure to the elastic element 24. The discharge nozzle 11 lies outside the sheathing tube 17, so that the fluid jet 2 can escape unhindered. As made clear by FIG. 7, which shows a cross-section through the fluid jet 2 along the line VII-VII in FIG. 6, the discharge nozzle 11 of FIG. 6 is configured as a thin slit (not shown in FIG. 6). Due to capillary forces, the fluid jet is thereby spread, as shown by FIG. 7, parallel to the guidance provided by the slit.

In FIG. 8, the shaft 16 is withdrawn and the spring element 26 is relaxed. The discharge nozzle 11 now lies within the elastic element 24 such that the fluid jet 2 is hindered on emergence from the water jet surgical instrument 10, resulting in the fluid jet 2 having the cross-section shown in FIG. 9 seen along the section line IX-IX in FIG. 8.

Figure 10:
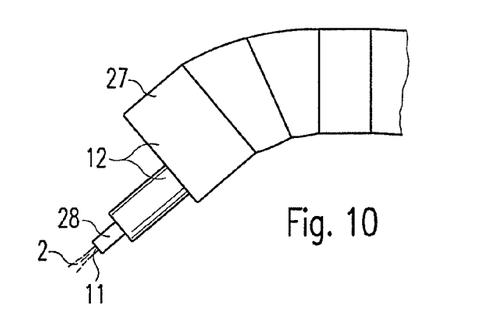
FIG. 10 is a schematic representation of another embodiment of the water jet surgical instrument (distal end) in a first adjustment position.
Figure 11:
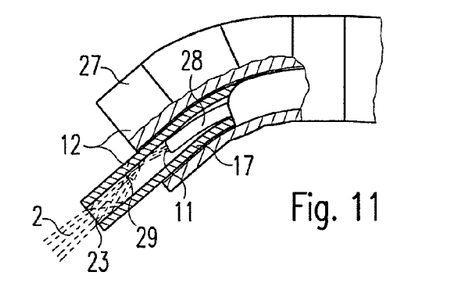
FIG. 11 is a schematic representation of the embodiment of FIG. 10 in a second adjustment position.

FIGS. 10 and 11 show the distal end 19 of the water jet surgical instrument 10 having an alternative embodiment of the jet shaping device 12. In this embodiment, the jet shaping device 12 consists of the shaft end portion 28, on which the discharge nozzle 11 is arranged, the sheathing tube 17 and a further sheathing 27. The sheathing 27 serves, in particular, to shape or curve the flexible sheathing tube 17.

In FIG. 10, the shaft end portion 28 with the discharge nozzle 11 is arranged partially outside the sheathing tube 17, so that the fluid jet 2 emerges in essentially laminar manner from the water jet surgical instrument 10.

In FIG. 11, the shaft end portion 28 is withdrawn into the sheathing tube 17, to which a curvature is imparted by the sheathing 27. The laminar jet from the discharge nozzle 11 impacts on an inner wall 29 of the sheathing tube 17, so that a fluid jet which is spread relative to that in FIG. 10 emerges from the sheathing tube 17. The energy of the fluid jet 2 emerging from the sheathing tube 17 depends on the distance of the discharge nozzle 11 from the sheathing tube aperture 23. This means that the shape and the energy of the fluid jet 2 can be influenced in a simple way.

Figure 12:
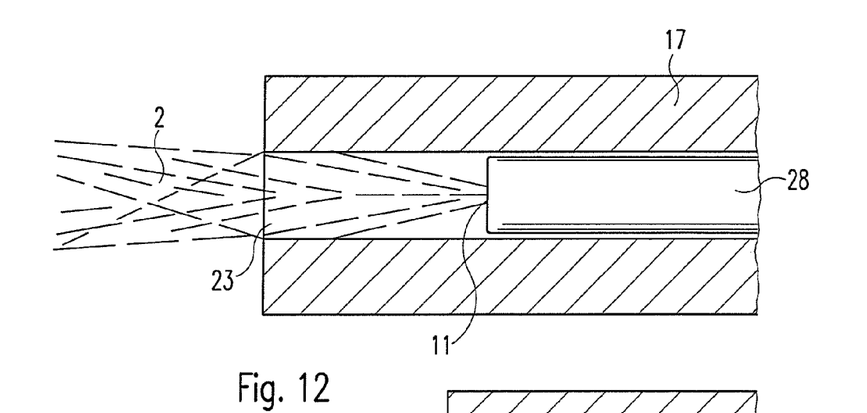
FIG. 12 illustrates another embodiment of the water jet surgical instrument (distal end) in a first and a second adjustment position.

FIG. 12 shows a particularly simple embodiment of the distal end 19 of the water jet surgical instrument 10. In this embodiment, the energy and spread of the jet 2 emerging from the water jet surgical instrument 10 is again adjusted purely through the position of the shaft end portion 28 and of the discharge nozzle 11. The principle applies here again that, as the distance of the discharge nozzle 11 (provided said nozzle is arranged within the sheathing tube 17) from the sheathing tube aperture 23 increases, the energy of the fluid jet 2 decreases.

Figure 13:
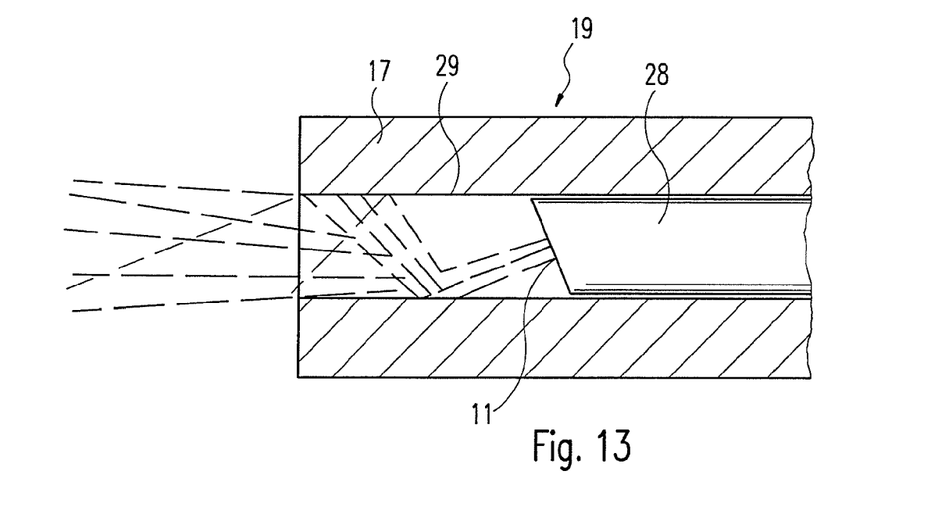
FIG. 13 is a schematic representation of another embodiment of the water jet surgical instrument (distal end).

FIG. 13 shows an embodiment similar to that of FIG. 12, except that in this case the shaft end portion 28 is configured with the discharge nozzle 11 such that the fluid jet impacts on the inner wall 29 of the sheathing tube 17 after emerging from the discharge nozzle 11 and thus loses energy.

Figure 14:
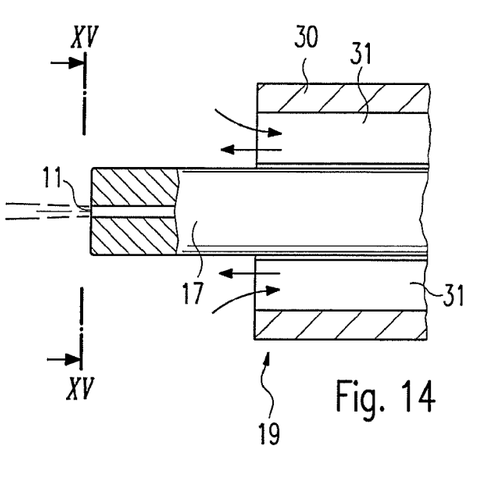
FIG. 14 is a schematic representation of another embodiment of the water jet surgical instrument (distal end).
Figure 15:
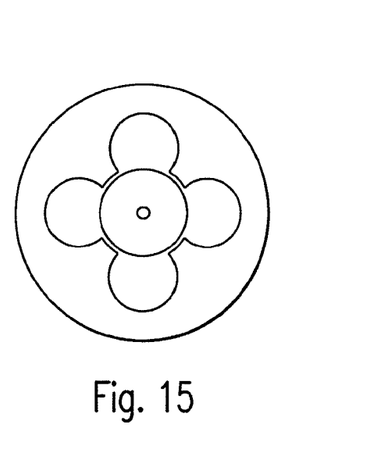
FIG. 15 is a cross-sectional view through the fluid jet along the line XV-XV in FIG. 14.

FIG. 14 shows another special embodiment of the distal end 19 of the water jet surgical instrument 10, wherein the sheathing tube 17 known from the previously described embodiments is arranged within an additional hollow body 30. The sheathing tube 17 extends from the hollow body 30 such that the discharge nozzle 11 lies outside the hollow body 30. Arranged between the hollow body 30 and the sheathing tube 17 are four channels 31, of which only two are shown in FIG. 14 (see also FIG. 15), in order to obtain fluid at a large volume flow rate for flushing out the operation site. The channels 30 can be used directly for cutting with the aid, for example, of high-frequency surgery for drawing away vapor and/or smoke, particularly also in order to prevent misting of the lens on an endoscope. FIG. 15 shows a cross-section through the emerging jet 2 along the line XV-XV in FIG. 14.

Figure 16:
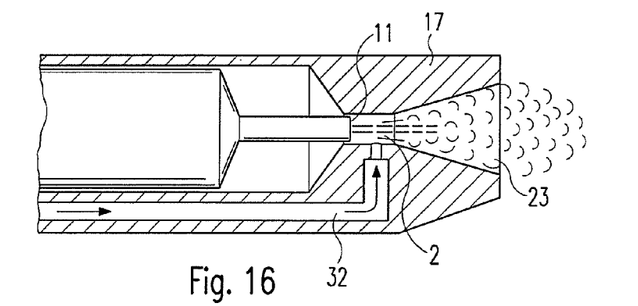
FIG. 16 illustrates another embodiment of the water jet surgical instrument (distal end).

FIG. 16 shows another embodiment of the distal end 19 of the water jet surgical instrument 10. The discharge nozzle 11 is arranged within the sheathing tube 17 in this case. The jet 2 emerging from the discharge nozzle is atomised and spread by mixing in a gaseous medium which is fed in via a feed channel 32, so that a more diffuse and energetically weakened fluid jet leaves the sheathing tube aperture 23. Alternatively, in place of a gaseous medium, a fluid medium can also be used for atomising the fluid jet 2 emerging from the discharge nozzle 11.

Figure 17:
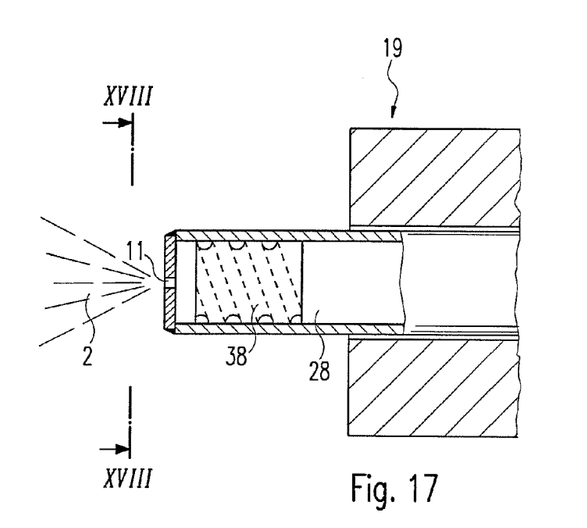
FIG. 17 is another embodiment of the water jet surgical instrument.
Figure 18:
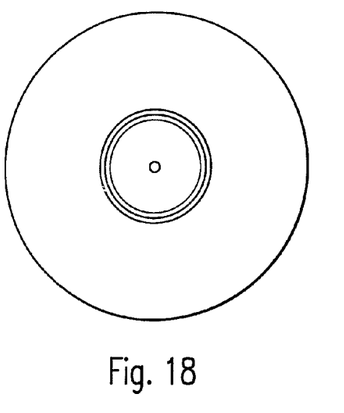
FIG. 18 is a cross-sectional view through the fluid jet (distal end) along the line XVIII-XVIII in FIG. 17.

FIG. 17 shows another preferred embodiment of the distal end 19 of the water jet surgical instrument 10. FIG. 18 shows a cross-section through the fluid jet 2 along the line XVIII-XVIII in FIG. 17. In the embodiment of FIG. 17, a swirl element 38, which is arranged within the sheathing sleeve 17, ensures that a forced twist direction is imposed upon the fluid jet 2. In the present embodiment, the swirl element 38 is configured as an internal screw thread.

As a consequence, droplets of the fluid jet 2 have a velocity component in a direction perpendicular to a mean spread direction of the jet. The jet spread or the energy of the fluid jet can be predetermined, for example, by means of the precise geometrical design of the swirl element 38 or can be adjusted by displacing the swirl element during use.

It should be emphasized at this point that the dimensioning of the internal screw thread 38 in FIG. 17 is not shown to scale. Depending on the desired spread, a person skilled in the art would adapt the dimensions of the internal screw thread 38 accordingly. It is also conceivable in principle to place the internal screw thread 38 according to FIG. 17 closer to the discharge nozzle 11 or to integrate said screw thread within the discharge nozzle 11.

Figure 19:
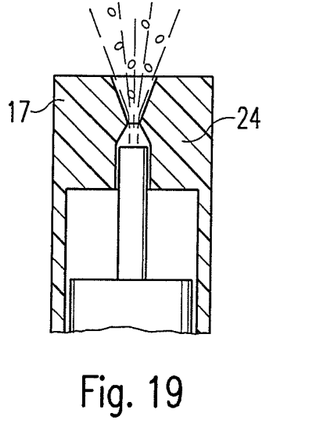
FIG. 19 is a schematic representation of another embodiment of the water jet surgical instrument (distal end).
Figure 20:
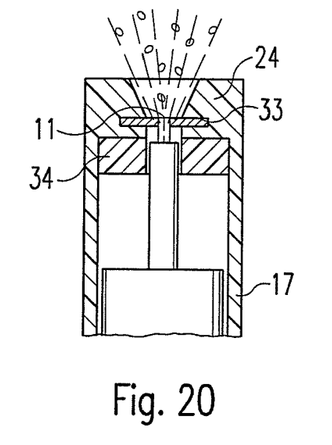
FIG. 20 is a schematic representation of another embodiment of the water jet surgical instrument (distal end).
Figure 21:
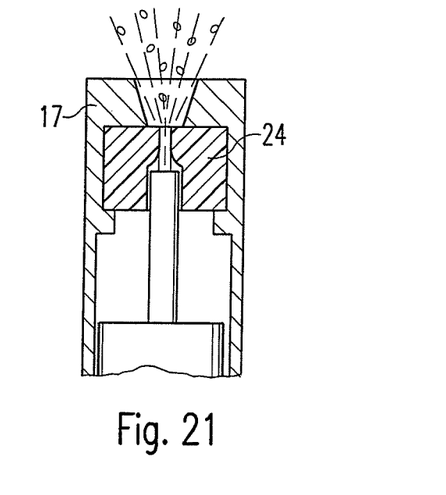
FIG. 21 is a schematic representation of another embodiment of the water jet surgical instrument (distal end).

FIGS. 19, 20 and 21 show embodiments of the elastic element(s) 24. The elastic element 24 can be made, for example, from foam material, rubber or the like. In FIG. 19, the elastic element 24 is a component part of the sheathing tube 17 and is made essentially in one piece therewith.

In FIG. 21, by contrast, the elastic element 24 is integrated in the sheathing tube 17, but is configured as a separate component.

In FIG. 20, an oscillating element 33, which is provided with a round or slit-shaped bore (not shown in FIG. 20), is responsible for the spreading and weakening of the fluid jet 2. Sealing elements 34 seal the discharge nozzle 11 against an inner region of the sheathing tube 17.

In FIGS. 22 to 27, various embodiments of the discharge nozzle 11 and of the sheathing tube aperture 23 are shown.

Figure 22:
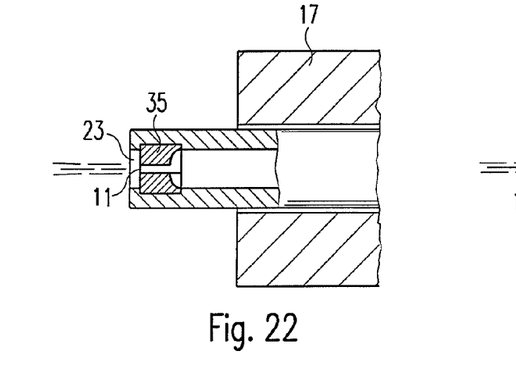
FIG. 22 is one embodiment of a discharge nozzle of the water jet surgical device.

In FIG. 22, the discharge nozzle 11 is configured for generating a superfine laminar fluid jet as a separate nozzle element or as a ruby 35.

Figure 23:
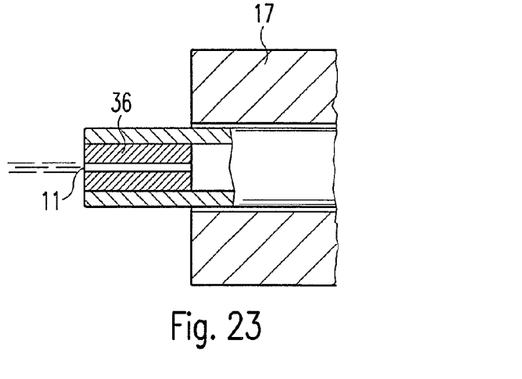
FIG. 23 is another embodiment of a discharge nozzle of the water jet surgical device.

In FIG. 23, the discharge nozzle 11 comprises a separately mounted thin capillary tube 36, also for generating a superfine laminar fluid jet.

Figure 24:
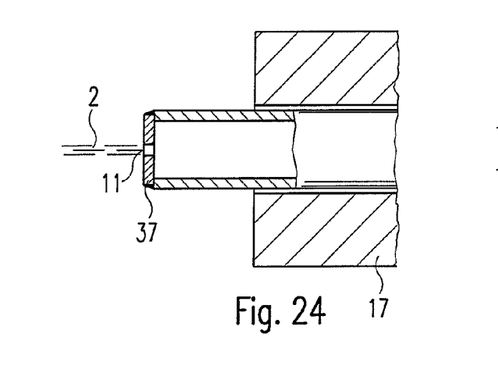
FIG. 24 is another embodiment of a discharge nozzle of the water jet surgical device.
Figure 25:
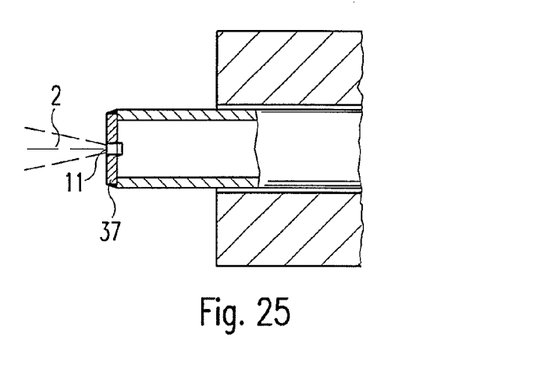
FIG. 25 is another embodiment of a discharge nozzle of the water jet surgical device.

In FIG. 24, the discharge nozzle 11 comprises a separately mounted thin aperture plate 37 for generating a superfine laminar fluid jet. A burr on the inside of the discharge nozzle 11 produces a turbulent fluid jet (see FIG. 25).

Figure 26:
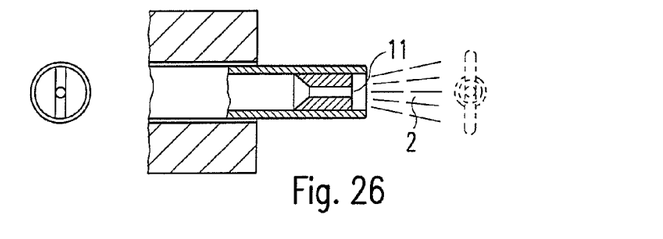
FIG. 26 is another embodiment of a discharge nozzle of the water jet surgical device.

In FIG. 26, the discharge nozzle 11 comprises a thin slit as the discharge aperture of the fluid jet. Due to the capillary forces, the fluid jet 2 is hindered at the edge on emergence and spreads out.

Figure 27:
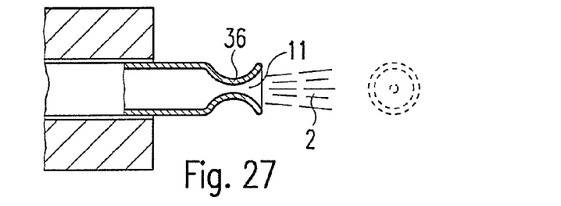
FIG. 27 is another embodiment of a discharge nozzle of the water jet surgical device.

FIG. 27 shows a discharge nozzle 11 which comprises a constricted capillary tube 36 as the discharge aperture for the fluid jet 2. Due to the capillary forces, the fluid jet 2 is slowed at one edge and a turbulent fluid jet is produced.

It should be noted at this point that all the aforementioned parts are claimed as essential to the invention both alone and in any combination, particularly the details shown in the drawings. Amendments thereof are the common practice of persons skilled in the art.

It should be noted in particular that the water jet surgical instrument 10 according to the invention can be produced both as a separate component and/or used as part of a high-frequency surgical instrument. In this case, the shaft 16 can also simultaneously function as a high-frequency electrode.

Alternatively, the water jet surgical instrument 10 described can also be used in combination with an argon plasma coagulation instrument.

The invention claimed is:

1. A water jet surgical instrument, comprising:
    a supply line for supplying a cutting fluid;
    a discharge nozzle for forming and discharging a fluid jet of the cutting fluid;
    a jet shaping device arranged relative to the discharge nozzle such that a spread angle and/or an emergence energy of a discharged fluid jet, emerging from a discharge aperture, is adjustable by the jet shaping device; and
    an adjusting element,
    wherein the discharge nozzle is movable via the adjusting element and within a sheathing tube comprising a sheathing tube aperture,
    wherein the jet shaping device is fixed relative to the sheathing tube,
    wherein, in a first position, the discharge nozzle extends distal of the jet shaping device and functions as the discharge aperture, and
    wherein, in a second position of the discharge nozzle, the discharge nozzle is fully retracted within the sheathing tube and the sheathing tube aperture functions as the discharge aperture, thereby setting an operating position of the discharge nozzle relative to the jet shaping device and setting the spread angle and/or the emergence energy of the discharged fluid jet.

2. The water jet surgical instrument according to claim 1, wherein the operating position of the discharge nozzle relative to the jet shaping device sets the spread angle of the discharged fluid jet.

3. The water jet surgical instrument according to claim 1, wherein the operating position of the discharge nozzle relative to the jet shaping device sets the emergence energy of the discharged fluid jet.

4. The water jet surgical instrument according to claim 1, wherein the jet shaping device is mounted in the sheathing tube and wherein the sheathing tube is flexible.

5. The water jet surgical instrument according to claim 1, wherein the jet shaping device comprises a swirl element which causes a twisting flow of the discharged fluid jet to thereby spread said discharged fluid jet and/or to reduce the emergence energy thereof.

6. The water jet surgical instrument according to claim 1, wherein the jet shaping device comprises a deflecting element, and wherein the deflecting element has at least two positions relative to the discharge nozzle, wherein, in a first of the at least two positions, the deflecting element is projecting at least partially into the discharged fluid jet in order to deflect or spread said discharged fluid jet and/or to reduce the emergence energy thereof and, in a second of the at least two positions, the deflecting element allows said discharged fluid jet to flow through the jet shaping device unchanged.

7. The water jet surgical instrument according to claim 1, wherein the jet shaping device comprises an air feed device, which feeds air into the discharged fluid jet in order to deflect and/or spread said discharged fluid jet and/or to reduce the emergence energy thereof.

8. The water jet surgical instrument according to claim 1, wherein the jet shaping device comprises a fluid feed device, which feeds fluid into the discharged fluid jet in order to deflect and/or spread said discharged fluid jet and/or to reduce the emergence energy thereof.

9. The water jet surgical instrument according to claim 1, wherein the jet shaping device comprises a Venturi nozzle for mixing in a gas or a fluid.

10. The water jet surgical instrument according to claim 1, wherein said water jet surgical instrument is configured for rinsing out an operation site.

11. The water jet surgical instrument according to claim 1, wherein said water jet surgical instrument is configured for cleaning an image recording device of an endoscope.

12. The water jet surgical instrument according to claim 1, wherein said water jet surgical instrument is configured to be insertable into a working channel of an endoscope.

13. The water jet surgical instrument according to claim 1, further comprising a nozzle spacer associated with the discharge nozzle in order to vary the distance of the discharge nozzle from a tissue to be treated.

14. A water jet surgical instrument, comprising:
    a supply line for supplying a cutting fluid;
    a discharge nozzle for forming and discharging a fluid jet of the cutting fluid;
    a jet shaping device arranged relative to the discharge nozzle such that a spread angle and/or an emergence energy of a discharged fluid jet, emerging from a discharge aperture, is adjustable by the jet shaping device; and
    an adjusting element,
    wherein the discharge nozzle is movable via the adjusting element and within a sheathing tube comprising a sheathing tube aperture,
    wherein, in a first position, the discharge nozzle extends distal of the jet-shaping device and functions as the discharge aperture,
    wherein, in a second position of the discharge nozzle, the discharge nozzle is fully retracted within the sheathing tube and the sheathing tube aperture functions as the discharge aperture, thereby setting an operating position of the discharge nozzle relative to the jet shaping device and setting the spread angle and/or the emergence energy of the discharged fluid jet, and wherein the jet shaping device comprises a swirl element which causes a twisting flow of the discharged fluid jet to thereby spread said discharged fluid jet and/or to reduce the emergence energy thereof.

15. The water jet surgical instrument according to claim 14, wherein the jet shaping device comprises a deflecting element, and wherein the deflecting element has at least two positions relative to the discharge nozzle, wherein, in a first of the at least two positions, the deflecting element is projecting at least partially into the discharged fluid jet in order to deflect or spread said discharged fluid jet and/or to reduce the emergence energy thereof and, in a second of the at least two positions, the deflecting element allows said discharged fluid jet to flow through the jet shaping device unchanged.

16. A water jet surgical instrument, comprising:
a supply line for supplying a cutting fluid;
a discharge nozzle for forming and discharging a fluid jet of the cutting fluid;
a jet shaping device arranged relative to the discharge nozzle such that a spread angle and/or an emergence energy of a discharged fluid jet, emerging from a discharge aperture, is adjustable by the jet shaping device; and
an adjusting element,
wherein the discharge nozzle is movable via the adjusting element and within a sheathing tube comprising a sheathing tube aperture,
wherein, in a first position, the discharge nozzle extends distal of the jet-shaping device and functions as the discharge aperture,
wherein, in a second position of the discharge nozzle, the discharge nozzle is fully retracted within the sheathing tube and the sheathing tube aperture functions as the discharge aperture, thereby setting an operating position of the discharge nozzle relative to the jet shaping device and setting the spread angle and/or the emergence energy of the discharged fluid jet, and
wherein the jet shaping device comprises a Venturi nozzle for mixing in a gas or a fluid.

17. The water jet surgical instrument according to claim 16, wherein the jet shaping device comprises a deflecting element, and wherein the deflecting element has at least two positions relative to the discharge nozzle, wherein, in a first of the at least two positions, the deflecting element is projecting at least partially into the discharged fluid jet in order to deflect or spread said discharged fluid jet and/or to reduce the emergence energy thereof and, in a second of the at least two positions, the deflecting element allows said discharged fluid jet to flow through the jet shaping device unchanged.

18. A water jet surgical instrument, comprising:
a supply line for supplying a cutting fluid;
a discharge nozzle for forming and discharging a fluid jet of the cutting fluid;
a nozzle spacer associated with the discharge nozzle in order to vary the distance of the discharge nozzle from a tissue to be treated;
a jet shaping device arranged relative to the discharge nozzle such that a spread angle and/or an emergence energy of a discharged fluid jet, emerging from a discharge aperture, is adjustable by the jet shaping device; and
an adjusting element,
wherein the discharge nozzle is movable via the adjusting element and within a sheathing tube comprising a sheathing tube aperture,
wherein, in a first position, the discharge nozzle extends distal of the jet-shaping device and functions as the discharge aperture,
wherein, in a second position of the discharge nozzle, the discharge nozzle is fully retracted within the sheathing tube and the sheathing tube aperture functions as the discharge aperture, thereby setting an operating position of the discharge nozzle relative to the jet shaping device and setting the spread angle and/or the emergence energy of the discharged fluid jet.

19. The water jet surgical instrument according to claim 18, wherein the jet shaping device comprises a deflecting element, and wherein the deflecting element has at least two positions relative to the discharge nozzle, wherein, in a first of the at least two positions, the deflecting element is projecting at least partially into the discharged fluid jet in order to deflect or spread said discharged fluid jet and/or to reduce the emergence energy thereof and, in a second of the at least two positions, the deflecting element allows said discharged fluid jet to flow through the jet shaping device unchanged.

* * * * *